(12) United States Patent
Mitamura

(10) Patent No.: US 10,750,929 B2
(45) Date of Patent: Aug. 25, 2020

(54) ENDOSCOPE DEVICE FOR GENERATING COLOR SUPERIMPOSED IMAGE

(71) Applicant: OLYMPUS CORPORATION, Tokyo (JP)

(72) Inventor: Motohiro Mitamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 240 days.

(21) Appl. No.: 15/701,653

(22) Filed: Sep. 12, 2017

(65) Prior Publication Data

US 2018/0000317 A1 Jan. 4, 2018

Related U.S. Application Data

(63) Continuation of application No. PCT/JP2015/058169, filed on Mar. 19, 2015.

(51) Int. Cl.
*A61B 1/00* (2006.01)
*G06T 11/00* (2006.01)
(Continued)

(52) U.S. Cl.
CPC .......... *A61B 1/00009* (2013.01); *A61B 1/043* (2013.01); *A61B 1/0638* (2013.01);
(Continued)

(58) Field of Classification Search
CPC combination set(s) only.
See application file for complete search history.

(56) References Cited

U.S. PATENT DOCUMENTS 6,346,940 B1 2/2002 Fukunaga
2003/0078477 A1* 4/2003 Kang ............... A61B 1/042
600/178

(Continued)

FOREIGN PATENT DOCUMENTS

EP 2 526 853 A1 11/2012
EP 2 636 359 A1 9/2013
(Continued)

OTHER PUBLICATIONS

International Search Report dated Feb. 21, 2017 issued in International Application No. PCT/JP2016/085898.
(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope device includes: an normal light image acquisition unit that acquires an normal light image; a special light image acquisition unit that acquires a special light image; a blended image generation unit that generates a blend image by combining one color component image from among a plurality of color component images constituting the normal light image and the special light image; and a superimposed image generation unit that generates a color superimposed image by combining the blended image with another color component image. The blended image generation unit generates the blended image by replacing a part of the pixels of the one color component image with the corresponding pixels of the special light image such that they are blended in a substantially uniform distribution over the entire blended image.

10 Claims, 11 Drawing Sheets

(51) Int. Cl.
*A61B 1/06* (2006.01)
*A61B 1/04* (2006.01)
*A61B 5/00* (2006.01)
*H04N 9/04* (2006.01)
*H04N 9/76* (2006.01)
*A61B 1/045* (2006.01)
*H04N 5/225* (2006.01)

(52) U.S. Cl.
CPC .......... *A61B 5/0071* (2013.01); *A61B 5/0084* (2013.01); *G06T 11/00* (2013.01); *H04N 9/045* (2013.01); *A61B 1/045* (2013.01); *H04N 9/76* (2013.01); *H04N 2005/2255* (2013.01)

(56) References Cited

U.S. PATENT DOCUMENTS

| | | | |
|---|---|---|---|
| 2003/0169354 A1* | 9/2003 | Aotsuka | H04N 5/335 348/272 |
| 2004/0155957 A1 | 8/2004 | Kobayashi | |
| 2006/0247535 A1* | 11/2006 | Sendai | A61B 1/00009 600/476 |
| 2007/0073104 A1 | 3/2007 | Iketani et al. | |
| 2007/0296841 A1* | 12/2007 | Nomura | H04N 9/045 348/273 |
| 2008/0088857 A1* | 4/2008 | Zimmer | H04N 1/56 358/1.6 |
| 2008/0170137 A1* | 7/2008 | Matsumoto | H04N 5/347 348/241 |
| 2010/0245616 A1* | 9/2010 | Yoshino | A61B 1/0638 348/223.1 |
| 2010/0289885 A1* | 11/2010 | Lu | H04N 5/2258 348/61 |
| 2011/0009702 A1* | 1/2011 | Morishita | A61B 1/00096 600/178 |
| 2011/0109761 A1 | 5/2011 | Shimotsu et al. | |
| 2012/0323072 A1 | 12/2012 | Ishihara | |
| 2012/0328175 A1 | 12/2012 | Watanabe | |
| 2013/0077862 A1* | 3/2013 | Nomura | H04N 9/045 382/167 |
| 2013/0193311 A1* | 8/2013 | Yoshida | H04N 9/045 250/208.1 |
| 2013/0208101 A1* | 8/2013 | Ono | A61B 1/00193 348/65 |
| 2014/0340497 A1 | 11/2014 | Shigeta | |
| 2015/0018690 A1* | 1/2015 | Kang | A61B 5/418 600/473 |
| 2015/0042774 A1 | 2/2015 | Sugano et al. | |
| 2015/0084986 A1* | 3/2015 | Lee | G09G 5/026 345/629 |
| 2015/0092032 A1* | 4/2015 | Kuramoto | A61B 1/00059 348/68 |
| 2016/0351609 A1* | 12/2016 | Borthakur | H04N 9/045 |
| 2017/0061230 A1 | 3/2017 | Sato | |
| 2017/0180641 A1* | 6/2017 | Yamada | G06T 7/38 |
| 2017/0280029 A1* | 9/2017 | Steiner | A61B 1/0005 |
| 2018/0000401 A1* | 1/2018 | Kang | A61B 5/418 |

FOREIGN PATENT DOCUMENTS

| | | |
|---|---|---|
| EP | 2 803 313 A1 | 11/2014 |
| EP | 3 207 855 A1 | 8/2017 |
| JP | H04-341232 A | 11/1992 |
| JP | H10-234664 A | 9/1998 |
| JP | 2004-236952 A | 8/2004 |
| JP | 2004-321244 A | 11/2004 |
| JP | 2007-075198 A | 3/2007 |
| JP | 2007-089840 A | 4/2007 |
| JP | 2011-101771 A | 5/2011 |
| JP | 2011-194164 A | 10/2011 |
| JP | 4799109 B2 | 10/2011 |
| JP | 2012-010962 A | 1/2012 |
| JP | 2014-221168 A | 11/2014 |
| JP | 2015-029841 A | 2/2015 |
| JP | 2015-194596 A | 11/2015 |
| WO | 2011/111619 A1 | 9/2011 |
| WO | 2012/132790 A1 | 10/2012 |
| WO | 2013/024788 A1 | 2/2013 |
| WO | WO 2013/024788 A | 2/2013 |
| WO | 2016/059977 A1 | 4/2016 |

OTHER PUBLICATIONS

International Search Report dated Mar. 21, 2017 issued in International Application No. PCT/JP2017/001050.
International Search Report dated May 19, 2015 issued in PCT/JP2015/058169.
Japanese Office Action dated Jan. 28, 2020 in Japanese Patent Application No. 2018-561754.

* cited by examiner

SMALL REGION

SMALL REGION

SMALL REGION

MINIMUM REPETITION UNIT

US 10,750,929 B2

ENDOSCOPE DEVICE FOR GENERATING COLOR SUPERIMPOSED IMAGE

CROSS-REFERENCE TO RELATED APPLICATIONS

This is a Continuation application of International Application No. PCT/JP2015/058169 filed on Mar. 19, 2015. The content of International Application No. PCT/JP2015/058169 is incorporated herein by reference in its entirety.

TECHNICAL FIELD

The present invention relates to an endoscope device.

BACKGROUND ART

As a conventional endoscope, an endoscope is known that is configured to acquire an normal light image such as a white light image and a special light image such as a fluorescent image, and the normal light image and the special light image thus acquired are displayed in a superimposing manner (see PTL 1 and 2, for example). As methods of superimposing the normal light image and the special light image, PTL 1 discloses a method in which such a special light image is added to one from among three color component images, i.e., the R component image, the G component image, and the B component image, that form the normal light image; and PTL 2 discloses a method in which a region of interest having high gradation value is extracted from the special light image, and the special light image in the region of interest is added to the normal light image.

CITATION LIST

Patent Literature

{PTL 1}
Japanese Patent No. 4799109
{PTL 2}
Japanese Patent No. 4394356

SUMMARY OF INVENTION

The present invention provides an endoscope device including: a normal light image acquisition unit that acquires a normal light image by capturing an image of a subject irradiated with a broadband visible light; a special light image acquisition unit that acquires a special light image by capturing an image of the subject irradiated with a narrow-band special light; a blended image generation unit that generates a blended image by combining one color component image from among a plurality of color component images constituting the normal light image and the special light image; and a superimposed image generation unit that generates a color superimposed image by combining the blended image generated by the blended image generation unit with another color component image from among the plurality of color component images, wherein the blended image generation unit generates the blended image by selecting a part of pixels from among the pixels of the one color component image, and by replacing the pixels of the selected part with corresponding pixels of the special light image, so that the pixels of the part of the one color component image are replaced with the corresponding pixels of the special light image such that the pixels of the one color component image and the pixels of the special light image are blended in a substantially uniform distribution over the entire blended image.

BRIEF DESCRIPTION OF DRAWINGS

FIG. 4 is a diagram showing a part of a blended image generated by the blended image generation unit shown in FIG. 2.

FIG. 5 is a diagram showing another example of the blended image generated by the blended image generation unit shown in FIG. 2.

DESCRIPTION OF EMBODIMENTS

First Embodiment

Description will be made with reference to FIGS. 1 through 5 regarding an endoscope device 1 according to a first embodiment of the present invention.

Figure 1:
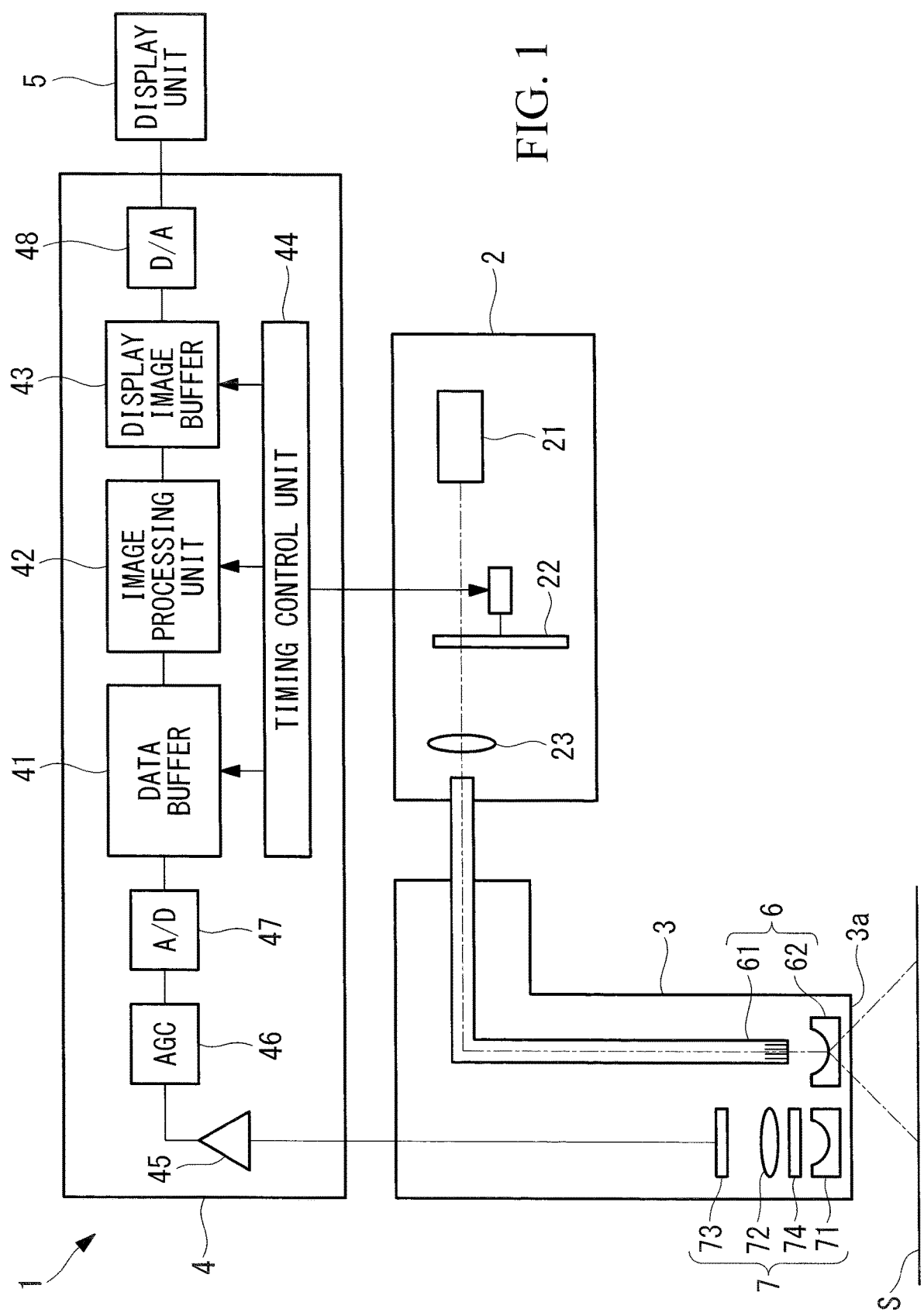
FIG. 1 is an overall configuration diagram showing an endoscope device according to a first embodiment of the present invention.

As shown in FIG. 1, the endoscope device 1 according to the present embodiment includes: a light source unit 2 that outputs normal light and excitation light (special light); an insertion unit 3 that can be inserted into the body, and that is configured to irradiate normal light and excitation light to a biological tissue S in the body and to acquire an image signal of the biological tissue S; a processor 4 that generates an image based on the image signal acquired by the insertion unit 3; and a display unit 5 that displays the image generated by the processor 4.

The light source unit 2 includes: a light source 21 that emits broadband light such as white light; a filter unit 22 configured to selectively transmit normal light and excitation light among the light emitted from the light source 21, and to allow the light thus selected to pass through; and a coupling lens 23 that converges the normal light or the excitation light after having passed through the filter unit 22. The filter unit 22 includes a turret including a normal light filter that selectively transmits the normal light that is broadband visible light, and an excitation light filter that selectively transmits the narrowband excitation light. The filter unit 22 rotationally drives the turret according to the control operation of a timing control unit 44 described later so as to alternately arrange the normal light filter and the excitation light filter on the optical axis of the light source 21. With such an arrangement, the normal light and the excitation light are alternately output from the light source unit 2.

The insertion unit 3 includes: an illumination unit 6 that irradiates the normal light and the excitation light output from the light source unit 2 toward the biological tissue (subject) S from a front end 3a of the insertion unit 3; and an imaging unit 7 provided at the distal end 3a of the insertion unit 3 for capturing an image of the biological tissue S.

The illumination unit 6 includes a light guide fiber 61 arranged over almost the entire length of the insertion unit 3 in the longitudinal direction, and an illumination optical system 62 provided on the distal end 3a of the insertion unit 3. The light guide fiber 61 guides the light converged by the coupling lens 23 from the base end to the front end thereof. The illumination optical system 62 diffuses the normal light and the excitation light emitted from the distal end of the light guide fiber 61 and irradiates the biological tissue S facing the distal end 3a of the insertion unit 3.

The image acquisition unit 7 includes an objective lens 71 that collects the light from the biological tissue S, a converging lens 72 that converges the light collected by the objective lens 71, and an imaging sensor 73 that captures an image formed by the light converged by the converging lens 72. Reference numeral 74 denotes an excitation light cutoff filter configured to block the excitation light and transmit the light in other wavelength ranges.

The imaging sensor 73 is, for example, a color CCD or a color CMOS. The imaging sensor 73 receives light incident from the objective lens 71, performs photoelectric conversion of the received light so as to generate an image signal, and transmits the generated image signal to the processor 4.

The processor 4 includes a data buffer 41 that temporarily holds the image signal received from the imaging sensor 73, an image processing unit 42 that performs image processing on the image signal received from the data buffer 41 so as to generate a superimposed image, a display image buffer 43 that temporarily holds the superimposed image output from the image processing unit 42, and a timing control unit 44 that synchronizes the operations of the buffers 41 and 43, the image processing unit 42, the filter unit 22, and the imaging sensor 73. Reference numeral 45 denotes an amplifier that amplifies the image signal output from the imaging sensor 73. Reference numeral 46 denotes a gain controller (AGC). Reference numeral 47 denotes an A/D converter that converts an image signal of an analog signal into an image signal of a digital signal. Reference numeral 48 denotes a D/A converter that converts an image signal of the digital signal of the superimposed image output from the display image buffer 43 into an image signal of the analog signal.

The timing control unit 44 instructs the imaging sensor 73 to perform exposure of normal light when the normal light filter is disposed on the output optical axis of the light source 21 and the biological tissue S is irradiated with normal light. When the excitation light filter is disposed on the output optical axis of the light source 21 and the biological tissue S is irradiated with the excitation light, the imaging sensor 73 is caused to perform fluorescence exposure, thereby alternately acquiring the normal light image signal and the fluorescent image signal.

The data buffer 41 temporarily holds the normal light image signal and the fluorescent image received from the imaging sensor 73, and transmits a pair of the normal light image signal and the fluorescent image signal to the image processing unit 42.

Figure 2:
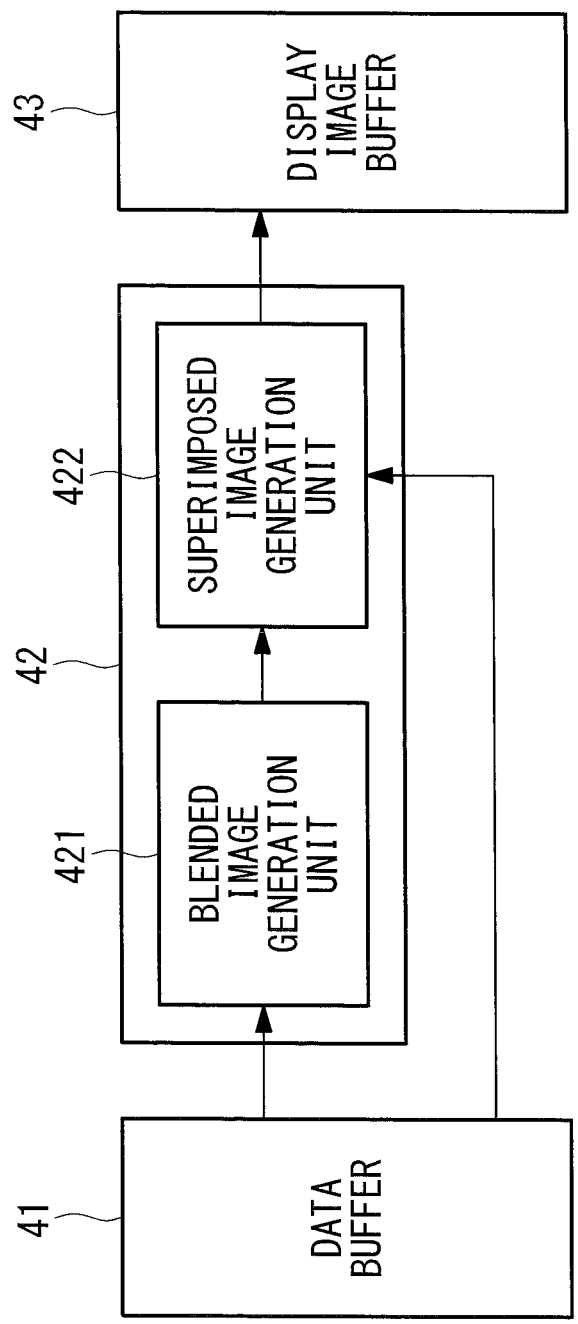
FIG. 2 is a configuration diagram showing an image processing unit in the endoscope device shown in FIG. 1.
Figure 3:
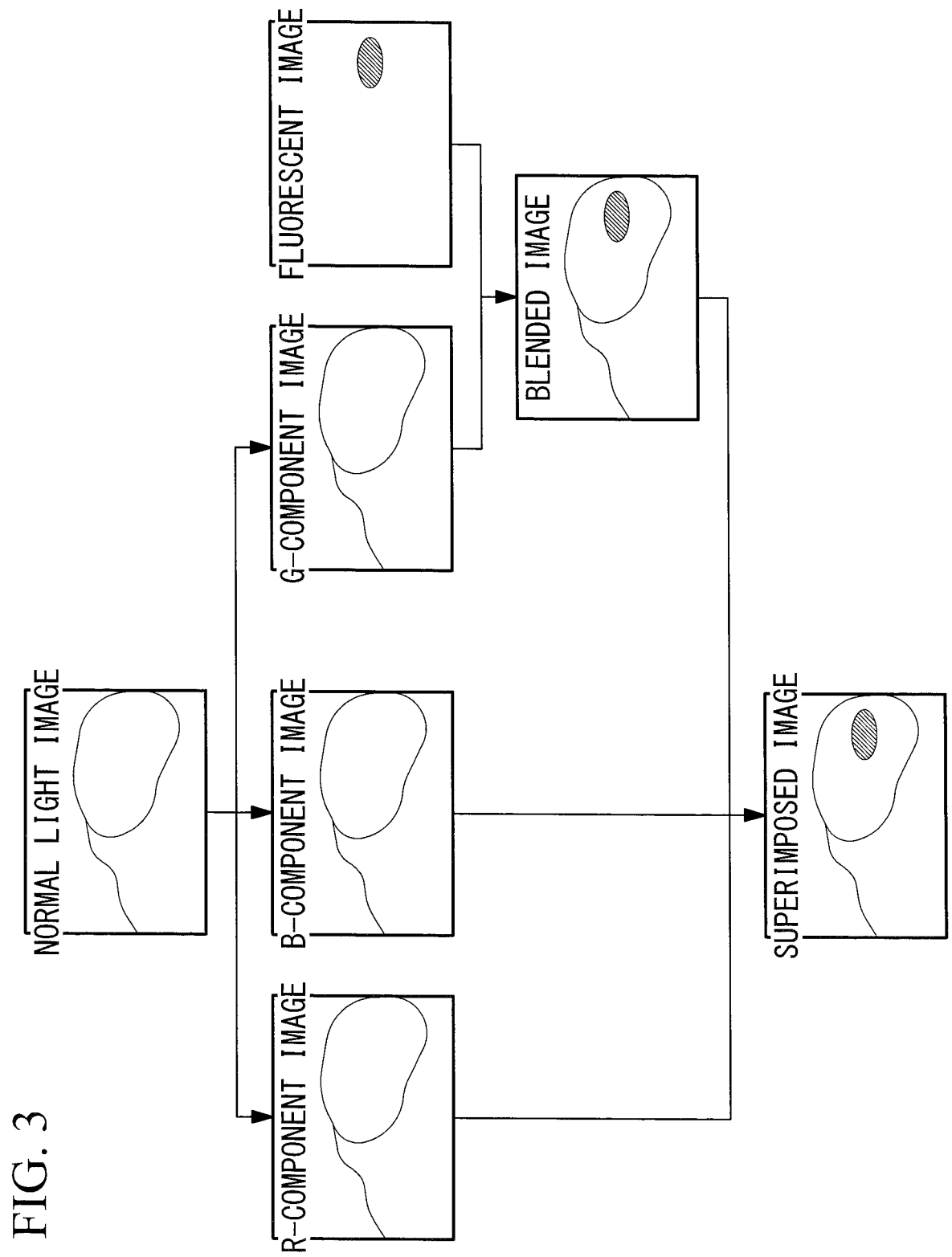
FIG. 3 is a diagram illustrating processing of a normal light image and a fluorescent image in the image processing unit of FIG. 2.

As shown in FIG. 2, the image processing unit 42 includes a blended image generation unit 421 and a superimposed image generation unit 422. FIG. 3 shows a step in which the superimposed image is generated by the image processing unit 42 from the normal light image and the fluorescent image. The normal light image signal obtained by capturing a broadband normal light image is constituting image signals of three color components, i.e., a red (R) image signal, a green (G) image signal, and a blue (B) image signal. The data buffer 41 transmits the G image signal and the fluorescent image signal to the blended image generation unit 421, and transmits the R image signal and the B image signal to the superimposed image generation unit 422.

The blended image generation unit 421 generates a G-component image based on the G-image signal received from the data buffer 41 and generates a fluorescent image based on the fluorescent image signal. The G-component image and the fluorescent image are each formed of a large number of pixels arrayed in the form of a two-dimensional array.

Figures 4, 5:
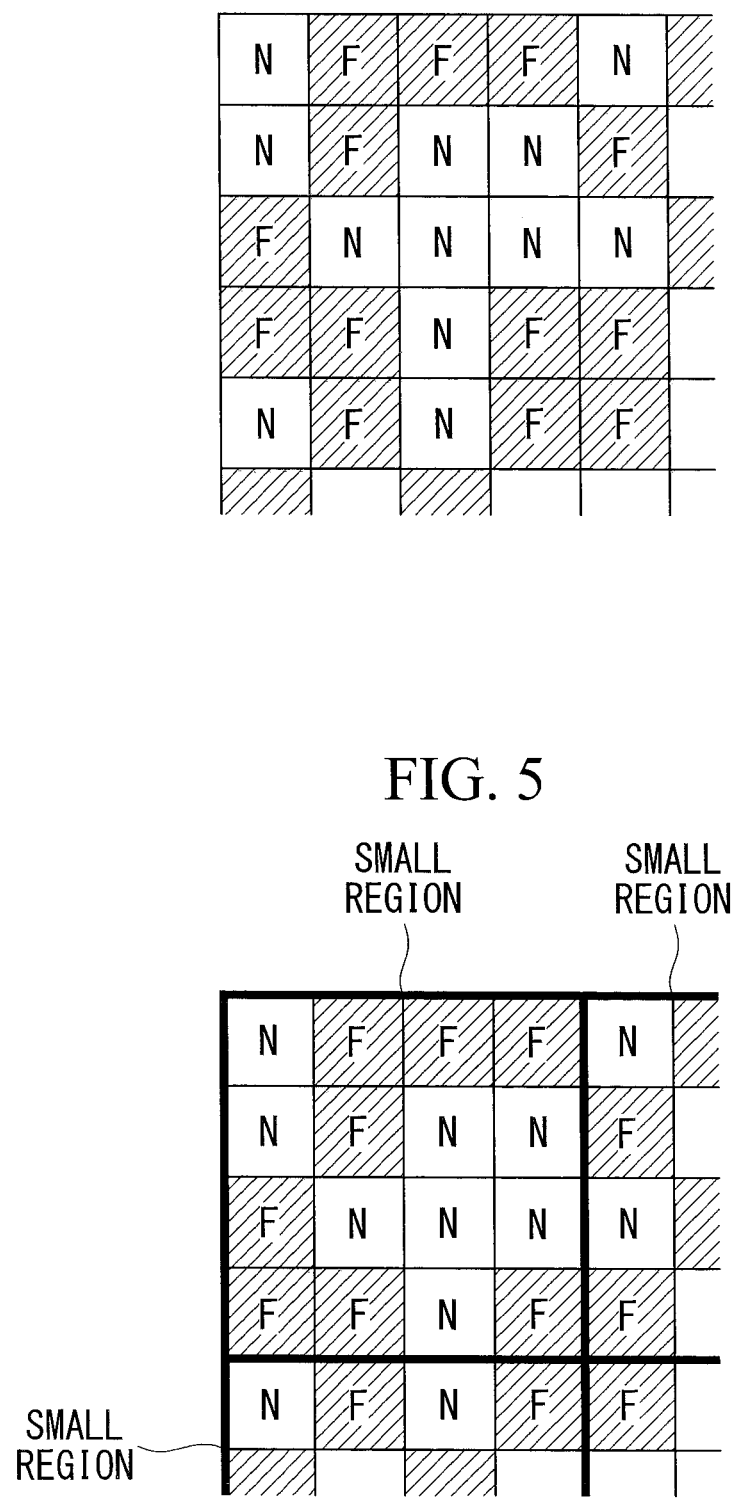

The blended image generation unit 421 selects a part of the pixels in a random manner from among all the pixels of the G-component image. It should be noted that the blended image generation unit 421 selects such a part of the pixels substantially uniformly from the entire G-component image so there is no bias in the position of the pixels selected in the G-component image. Subsequently, the blended image generation unit 421 replaces each of the selected pixels with the pixels of the fluorescent image at the same positions as the pixels. As shown in FIG. 4, such an arrangement generates a blended image in which the pixels of the G-component image and the pixels of the fluorescent image are mixed in a substantially uniform distribution over the entire blended image. In FIG. 4, "N" represents a pixel of the normal light image, and "F" represents a pixel of the fluorescent image. The blended image generation unit 421 transmits the generated blended image to the superimposed image generation unit 422.

The superimposed image generation unit 422 uses the blended image received from the blended image generation unit 421 as a substitution for the G-component image and by combining the blended image received from the blended image generation unit 421 and other color component images (the R-component image and the B-component image) received from the data buffer 41, generates a superimposed image configured as a color image. The superimposed image generation unit 422 transmits the generated superimposed image to the display image buffer 43.

The display image buffer 43 temporarily holds the superimposed image received from the superimposed image generation unit 422, and outputs the superimposed image thus held to the display unit 5 via the D/A converter 48 at regular time intervals.

Next, description will be made regarding the operation of the endoscope device 1 having such a configuration. Before the biological tissue S is observed using the endoscope device 1 according to the present embodiment, the biological tissue S is administered by a fluorescent material that will accumulate in the lesions.

First, the insertion unit 3 is inserted into the body such that its distal end 3a is disposed facing the biological tissue S, and the light source unit 2 operates such that the normal light and the excitation light are alternately irradiated onto the biological tissue S from the distal end 3a of the insertion unit 3.

When the normal light is irradiated to the biological tissue S, the normal light reflected by the surface of the biological tissue S is collected by the objective lens 71. The normal light collected by the objective lens 71 is converged on the imaging surface of the imaging sensor 73. The normal light image thus converged is acquired by the imaging sensor 73 as a normal light image signal.

On the other hand, when the excitation light is irradiated onto the biological tissue S, the fluorescent substance contained in the lesion is excited by the excitation light, thereby generating fluorescent light, and a part of the fluorescent light and the excitation light are collected by the objective lens 71. Only the fluorescent light is extracted by the excitation light cut filter 74 from the fluorescent light and the excitation light thus collected by the objective lens 71. The fluorescent light thus extracted is converged on the imaging surface of the imaging sensor 73 by the converging lens 72, and is acquired by the imaging sensor 73 as a fluorescent image signal. The normal light image signal and the fluorescent image signal alternately acquired by the imaging sensor 73 as described above are transmitted to the processor 4.

In the processor 4, the normal light image signal and the fluorescent image signal are input to the data buffer 41 via the amplifier 45, the AGC 46, and the A/D converter 47, and a pair of the normal light image signal and the fluorescent image signal are input from the data buffer 41 to the image processing unit 42. In this stage, the normal light image is separated into a G image signal, an R image signal, and a B image signal. The G image signal is input to the blended image generation unit 421 together with the fluorescent image signal. The R image signal and the B image signal are input to the superimposed image generation unit 422.

The blended image generation unit 421, by replacing a part of the pixels of the G-component image with the pixels of the fluorescent image generates a blended image, in which the G-component image pixels and the fluorescent image pixels are blended in a substantially uniform distribution over the entire image. The blended image includes both the biological tissue S image in the G-component image and the biological tissue S image in the fluorescent image. The generated blended image is color synthesized with the R-component image and the B-component image by the superimposed image generation unit 422, so as to generate a superimposed image. The superimposed image thus generated is sequentially output to the display unit 5 from the display image buffer 43 via the D/A converter 48 at regular intervals. As a result, the display unit 5 displays the superimposed image as a live moving image.

In this case, according to the present embodiment, the blended image is an image blended such that the pixels of the G-component image and the pixels of the fluorescent image are mixed in a substantially uniform distribution over the entire blended image. The fluorescent image is synthesized substantially uniformly over the entire blended image regardless of the gradation values. Accordingly, among the fluorescent image regions, not only the fluorescent light regions having sufficiently high gradation values, but also the fluorescent image regions having relatively low gradation values are synthesized with the blended image. Such an arrangement provides an advantage of allowing the superimposed image to be generated in which all the fluorescent image regions that are to be noticed for the observer are displayed.

Furthermore, the gradation values of each pixel of such a blended image is the gradation values of the pixel of the G-color component image or the gradation values of the corresponding pixel of the fluorescent image itself. In a case of the superimposed image color synthesized using such a blended image, there is an advantage that it is possible to reproduce a color tone substantially the same color tone as that of the normal light image. Moreover, even if the fluorescent image has a low S/N ratio, and the fluorescent image contains noise, by blending the pixels of the fluorescent image and the pixels of the G-component image without noise, the noise is reduced in the blended image. That is to say, such an arrangement has an advantage of obtaining a superimposed image with less noise.

It should be noted that, in the present embodiment, as shown in FIG. 5, the blended image generation unit 421 may divide the G-component image into small regions each having a predetermined number of pixels. Also, the blended image generation unit 421 may select, in a random manner for each small region, a predetermined number of pixels to be replaced with the pixels of the fluorescent image. In an example shown in FIG. 5, each small region is configured as a (4×4) pixels array. In each small region, eight pixels represented by "N" are replaced with the pixels represented by "F". With such an arrangement, it is possible to generate a blended image in which the pixels represented by "N" and the pixels represented by "F" are blended with even more uniform distribution over the entire image. In this case, the blended image generation unit 421 may determine the pixels to be replaced with "F" pixels for each small region. Alternatively, the blended image generation unit 421 may select, in a random manner, the pixels to be replaced with the "F" pixels from the pixel array that form each small region, so as to determine a pattern. The determined identical pattern may be applied to all the small regions. In this case, in the blended image, the small regions having the same arrangements of the "N" pixels and the "F" pixels repeated in the row direction and in the column direction.

Second Embodiment

Next, description will be made with reference to FIG. 6 regarding an endoscope device according to a second embodiment of the present invention.

The point of difference from the first embodiment is that, with the endoscope device according to the present embodiment, the blended image generation unit (blend pattern setting unit) 421 selects the pixels of the G-component image to be replaced with the corresponding pixels of the fluorescent image according to a predetermined blend pattern, instead of selecting the pixels in a random manner.

The blend pattern generation unit 421 stores a blend pattern that defines the array of the "N" pixels of the G-component image, and the "F" pixels of the fluorescent image. As shown in FIG. 6, the blend pattern is configured as a square grid array pattern in which the "N" pixels and "F" pixels are arrayed in a checkered pattern in one-pixel units alternately in the row direction and the column direction, where single "N" pixels are located next to single "F" pixels in the row and column directions. From among all the pixels of the G-component image, the blended image generation unit 421 replaces the pixels that correspond to the "F" pixels of the blend pattern with the pixels of the fluorescent image, so as to generate the blended image.

Other configurations of the present embodiment are the similar to those of the first embodiment.

According to the present embodiment, by arranging the "N" pixels of the G-component and the "F" pixels of the fluorescent image in a square grid array in one-pixel units, the noise included in the fluorescent image is effectively reduced in the blended image. Such an arrangement provides an advantage of generating the superimposed image with further reduced noise. Furthermore, there is an advantage that, in a superimposed image color synthesized by using the blended image in which the "N" pixels of the G-component image is more uniformly distributed, a color tone that is even closer to that of the normal light image can be reproduced.

It should be noted that description has been made in the present embodiment regarding such a square grid array pattern in which the "N" pixels and "F" pixels are arrayed in the form of a checkered pattern in one-pixel units. Also, a square grid array pattern in which "N" pixels and "F" pixels are arrayed in the form of a checkered pattern in a plurality of square arrayed pixel units may be used. For example, "N" of four pixels having a square array of (2×2) pixels and "F" of four pixels having a square array of (2×2) pixels may be alternately arrayed in the row direction and in the column direction.

Third Embodiment

Next, description will be made with reference to FIGS. 7 and 8 regarding an endoscope device according to a third embodiment of the present invention.

The endoscope according to the present embodiment is common to the second embodiment in that the blended image generation unit 421 selects the pixels to be replaced with the pixels of the fluorescent image according to a predetermined blend pattern. The point of difference from the second embodiment is that the blended image generation unit 421 selects a blend pattern that differs from that of the second embodiment.

Figures 6, 7:
FIG. 6 is a diagram showing a blend pattern used in the blended image generation unit in the endoscope device according to a second embodiment of the present invention.
FIG. 7 is a diagram showing a blend pattern used in the blended image generation unit in the endoscope device according to a third embodiment of the present invention.

In the present embodiment, as shown in FIG. 7, the blend pattern is configured as a periodic array pattern obtained by periodically arraying the "N" pixels and the "F" pixels alternately in the row direction and in the column direction in arbitrary units of one pixel or several pixels. In the blend pattern, the alternate periods of the "N" pixels and the "F" pixels in the row direction and the alternate periods of the "N" pixels and the "F" pixels in the column direction are different from each other. In the example shown in FIG. 7, the three "N" pixels and one "F" pixel are alternately arrayed in the row direction, and one "N" pixel and one "F" pixel are alternately arrayed in the column direction. Accordingly, a minimum repetition unit of the period alternating "N" and "F" pixels is four pixels in the row direction and two pixels in the column direction. Furthermore, in such a minimum repetition unit of the blend pattern, the number of "F" pixels is equal to or larger than the number of "N" pixels. When the number of "F" pixels is smaller than the number of "N" pixels in the minimum repetition unit, such an arrangement reduces the effect of emphasizing the fluorescent region (described later) in the superimposed image.

When a superimposed image is generated using the blended image generated according to such a blend pattern, periodic patterns corresponding to the array of "F" in the blend pattern are displayed in green in the superimposed image. In particular, in a case in which a fluorescent region has high gradation values in the blended image, such a green pattern is clearer in such a region. Accordingly, as compared with an arrangement in which the entire fluorescent region is displayed in a uniform green color, the distinguishability of the fluorescent region in the superimposed image can be improved. On the other hand, in the region other than the fluorescent region, since the region has low gradation values in the blended image, the green pattern becomes unclear to the extent that it cannot be visually recognized.

In the present embodiment, the blend pattern used in the blended image generation unit 421 may be changed over time, so that the pattern dynamically changes in the superimposed image.

Figure 8:
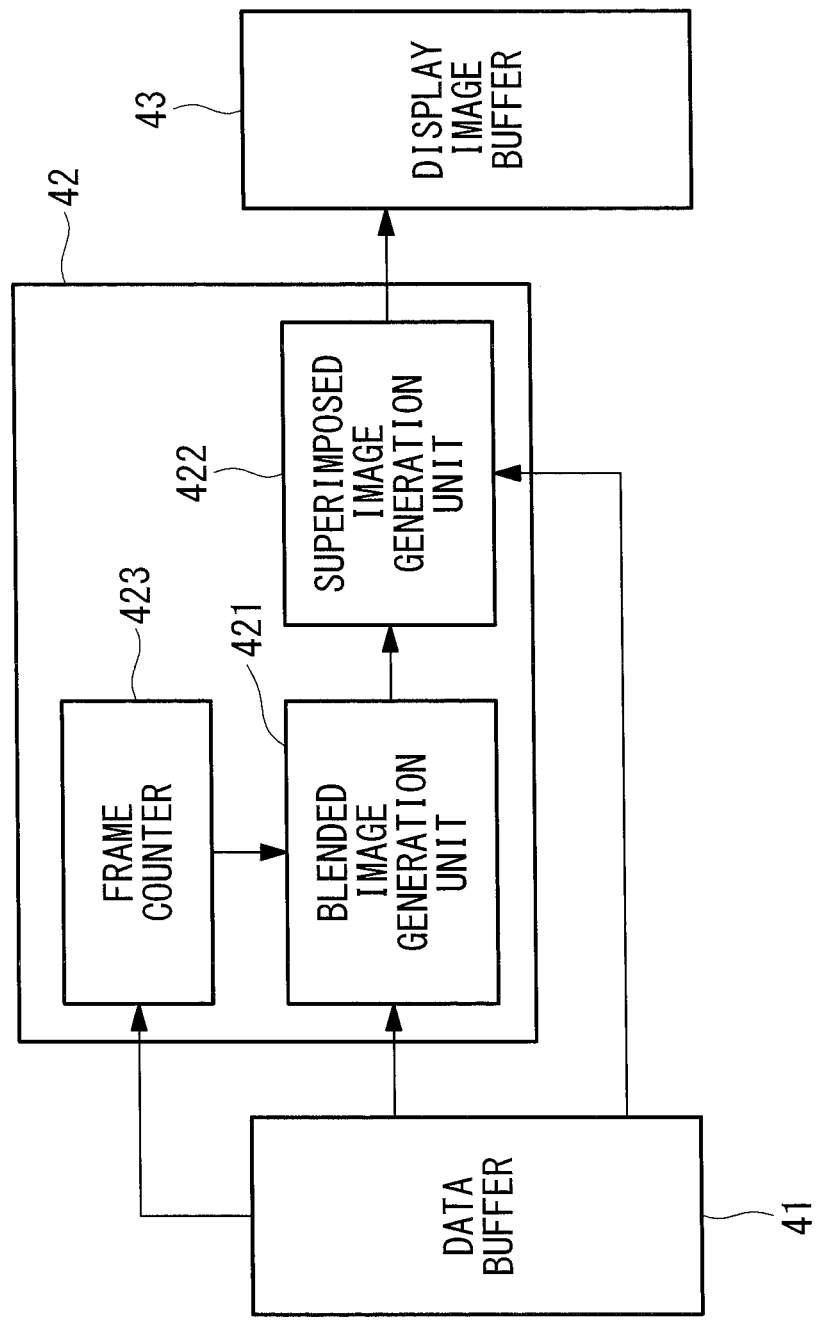
FIG. 8 is a configuration diagram showing an image processing unit in a modification of the endoscope device according to the third embodiment of the present invention.

Specifically, as shown in FIG. 8, a frame counter 423 is further provided in order to count the number of images input from the data buffer 41 to the blended image generation unit 421. The blended image generation unit 421 stores a plurality of types of blend patterns, and the blended image generation unit 421 is configured to change the blend pattern to be used for generating the blended image according to the count number obtained by the frame counter 423. For example, when the count number is an even number, the blended image generation unit 421 uses a first pattern. When the count number is an odd number, the blended image generation unit 421 uses a second pattern that differs from the first pattern. Thus, since the green pattern displayed in the fluorescent region of the superimposed image dynamically changes, the distinguishability of the fluorescent region can be further improved.

Fourth Embodiment

Next, description will be made with reference to FIGS. 9 through 11 regarding an endoscope device according to a fourth embodiment of the present invention.

Figure 9:
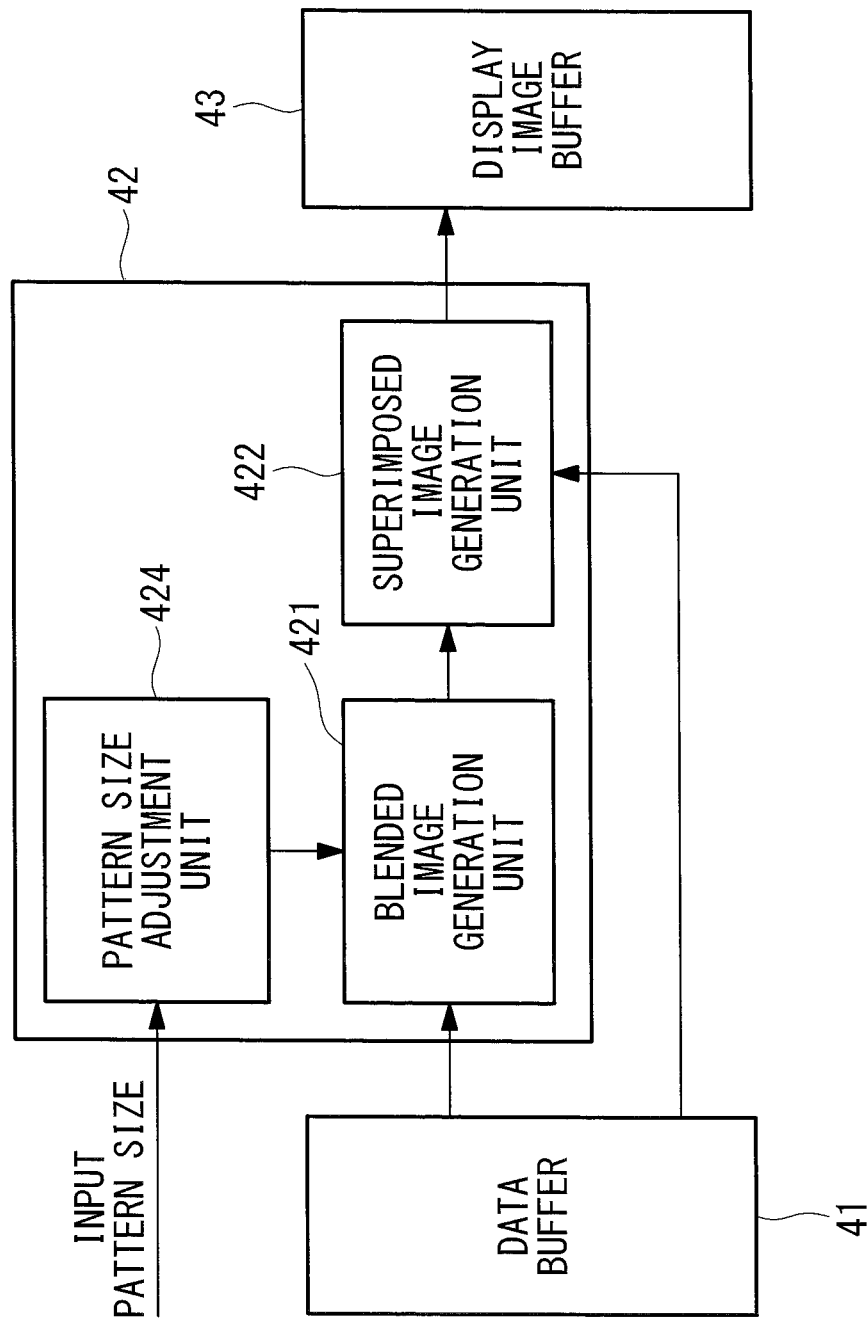
FIG. 9 is a configuration diagram showing the image processing unit in the endoscope device according to a fourth embodiment of the present invention.

The point of difference from the first embodiment is that, as shown in FIG. 9, the endoscope device according to the present embodiment further includes a pattern size adjustment unit (blend pattern setting unit) 424.

In the present embodiment, as with the second embodiment, the blended image generation unit 421 selects the pixels to be replaced with the pixels of the fluorescent image according to a predetermined blend pattern. It should be noted that, in the present embodiment, the blended image generation unit 421 stores a plurality of blend patterns having the same pattern with different pattern sizes.

Figure 10:
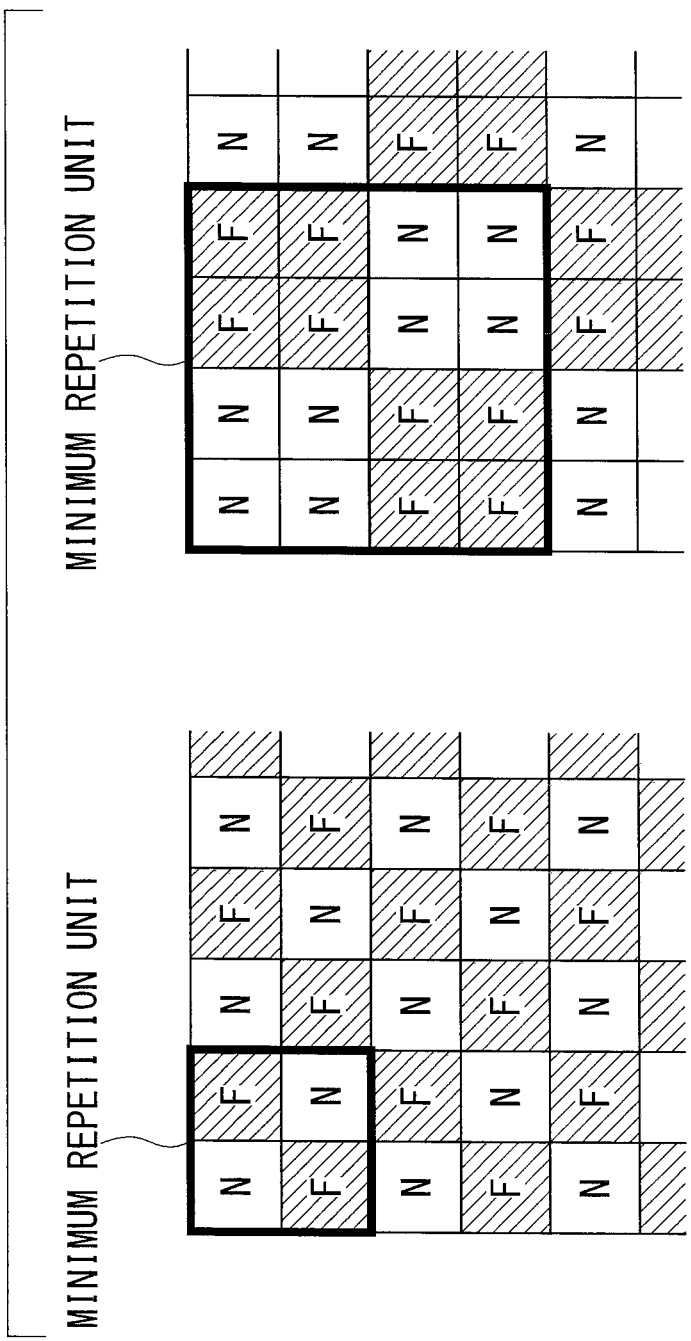
FIG. 10 is a diagram showing a blend pattern used in the blended image generation unit shown in FIG. 9.

Specifically, as shown in FIG. 10, the blended image generation unit 421 is provided with a plurality of blend patterns, each configured as a square grid array pattern of the "N" pixels and the "F" pixels, in which the number of pixels of the minimum repetition units respectively having different numbers of pixels are stored. For example, as shown in the diagram on the left in FIG. 10, in one blend pattern, the "N" pixels and the "F" pixels are alternately arranged in the row direction and in the column direction in one-pixel units, and the minimum repetition unit is four pixels. In another blend pattern, as shown in the right-side diagram shown in FIG. 10, "N" of four pixels having a square array of (2×2) pixels and "F" of four pixels having a square array of (2×2) pixels is alternately arrayed in the row direction and in the column direction, and the minimum repetition unit is sixteen pixels.

The pattern size adjustment unit 424 is configured to allow the observer to input a pattern size using a not shown input device. The pattern size corresponds to the number of pixels in the minimum repetition unit in the blend pattern. For example, the pattern size adjustment unit 424 is configured to allow the observer to specify the pattern size such as "2×2" or "4×4".

The blended image generation unit 421 selects a blend pattern of the pattern size specified for the pattern size adjustment unit 424 and generates the blended image using the selected blend pattern.

The other configurations of the present embodiment are similar to those described in the first embodiment.

In the superimposed image, a checkered pattern that corresponds to an "F" pixel array in the blend pattern is displayed in green. In the present embodiment, by increasing the pattern size, it is possible to increase the size of such a checkered pattern, thereby providing improved distinguishability of the fluorescent region in the superimposed image. On the other hand, in a case when the pattern size is set to the extent that the checkered pattern cannot be visually recognized, i.e., such that the pattern size appears to be uniform green, it is possible to display the fluorescent region in a natural manner in the superimposed image. As described above, such an arrangement has an advantage that it is possible to adjust the distinguishability of the fluorescent region according to a need of the observer.

It should be noted that, in the present embodiment, a periodic array pattern as described in the third embodiment may be employed instead of a periodic array pattern.

Figure 11:
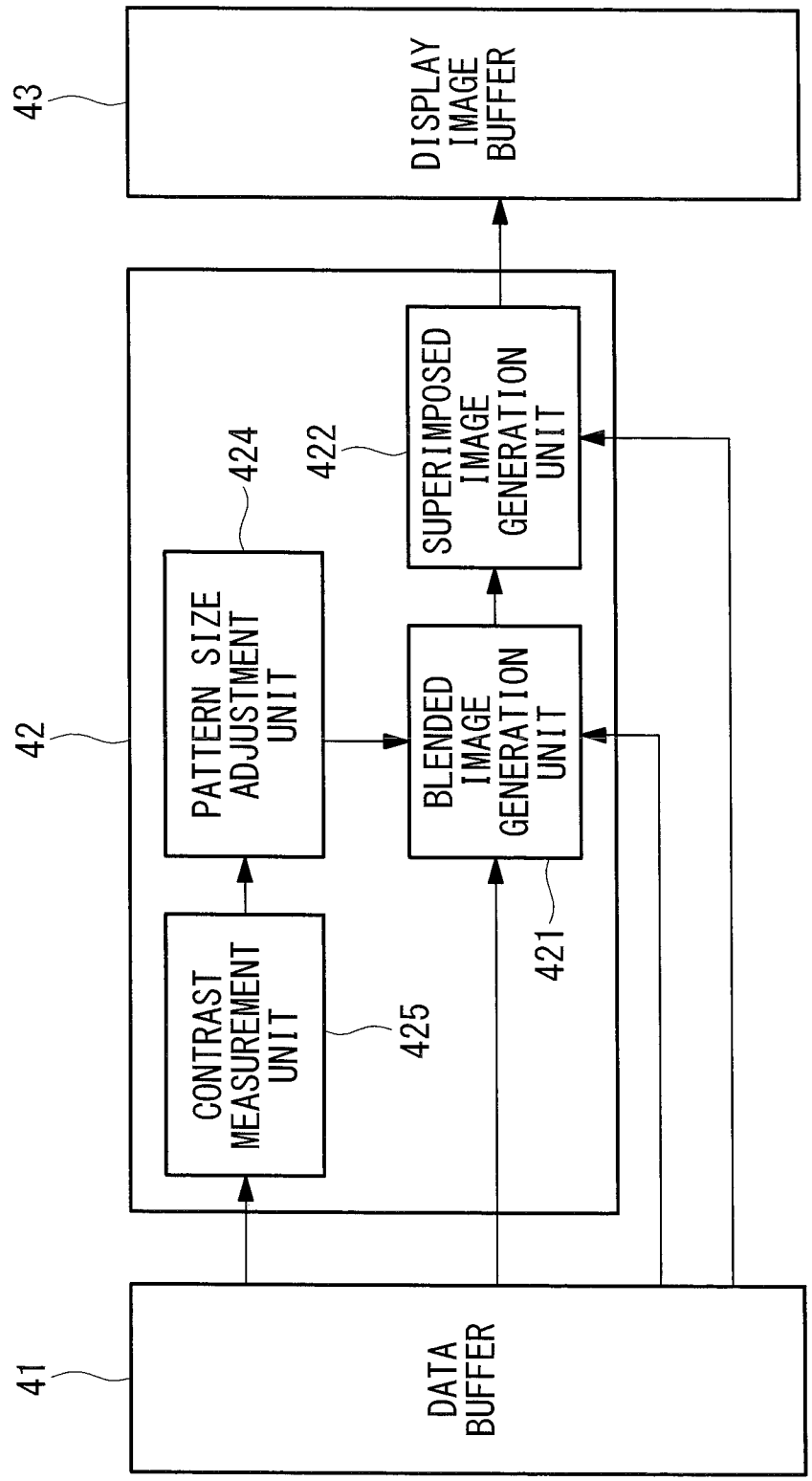
FIG. 11 is a configuration diagram showing the image processing unit in a modification of the endoscope device according to the fourth embodiment of the present invention.

Also, in the present embodiment, as shown in FIG. 11, the endoscope device may further include a contrast measurement unit 425 that measures the contrast of brightness of the fluorescent image. The pattern size adjustment unit 424 may automatically determine the pattern size based on the contrast level measured by the contrast measurement unit 425.

The contrast measurement unit 425 measures the contrast of the fluorescent image based on the width of the histogram of the gradation values of the fluorescent image, for example. When the gradation values of the fluorescent region in the fluorescence image is high, the fluorescent image contrast of brightness between the fluorescent region and the non-fluorescent region increases and the width of the histogram increases. On the other hand, when the gradation values of the fluorescent region in the fluorescent image is low, the fluorescent image contrast of brightness between the fluorescent region and the non-fluorescent region becomes low and the width of the histogram becomes small.

The pattern size adjustment unit 424 sets the pattern size so as to be larger as the contrast of the fluorescent image is lower.

In a case in which the fluorescent region has low gradation values in the fluorescent image, the distinguishability of the fluorescent region in the superimposed image becomes low. With the present modification, when the fluorescent image has a low contrast of brightness, the pattern size is automatically changed to a large pattern size, thereby providing improved distinguishability of the fluorescent region in the superimposed image. As described above, by changing the pattern size based on the contrast of brightness of the fluorescent image, it is possible to optimally and automatically adjust the distinguishability of the fluorescent region in the superimposed image.

Further, in the present embodiment, the pattern size of the blend pattern is changed uniformly in the entire blended image. Alternatively, the pattern size may be determined for each region of the blended image.

For example, to the region in the fluorescent image where the gradation values are less than a predetermined threshold value, a pattern size larger than the pattern size in the region where the gradation value is equal to or larger than the predetermined threshold value may be applied. With such an arrangement, it is possible to display a large pattern on a fluorescent region which is dark and has low distinguishability in the superimposed image, thereby improving the distinguishability.

Also, in the present embodiment, the endoscope device may include a brightness measurement unit (not shown) that measures the brightness level of the fluorescent image, instead of the contrast measurement unit 425, and the pattern size adjustment unit 424 may adjust the pattern size based on the brightness level of the fluorescent image measured by the brightness measurement unit.

The brightness measurement unit calculates, as the brightness level, the average value of the gradation values of all the pixels of the fluorescent image, for example. The pattern size adjustment unit 424 sets the pattern size to be larger as the brightness of the fluorescent image measured by the brightness measuring unit is lower. With such an arrangement, when the fluorescent image is dark, the pattern displayed on the superimposed image becomes large, thereby providing improved distinguishability of the fluorescent region in the superimposed image.

Fifth Embodiment

Figure 12:
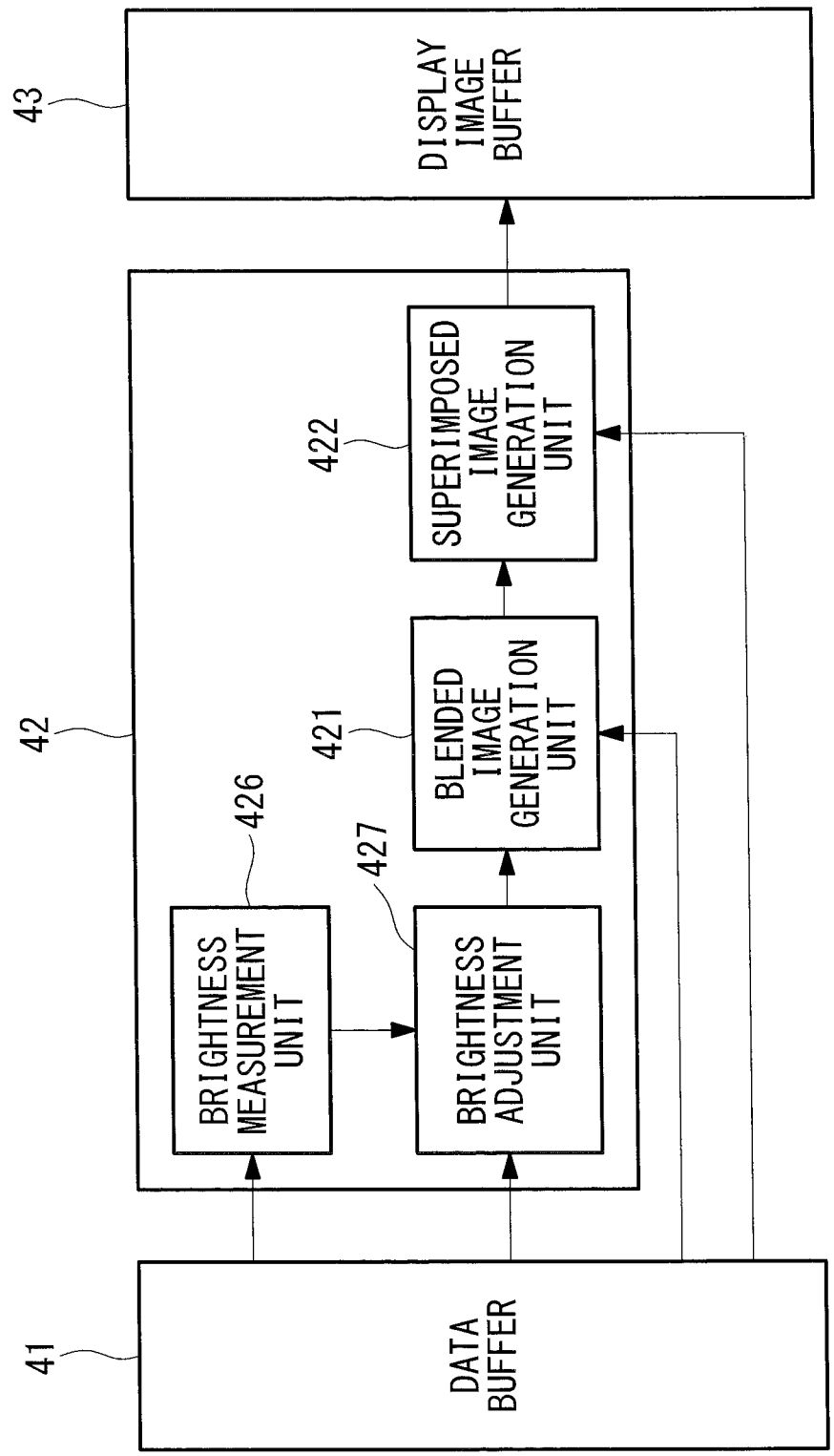
FIG. 12 is a configuration diagram showing the image processing unit in the endoscope device according to a fifth embodiment of the present invention.

Next, description will be made with reference to FIG. 12 regarding an endoscope device according to a fifth embodiment of the present invention.

The endoscope device according to the present embodiment is configured as a modification of any one of the first through fourth embodiments described above. As shown in FIG. 12, the endoscope device further includes a brightness measurement unit 426 that measures the brightness of the fluorescent image and a brightness adjustment unit 427 that adjusts the brightness of the fluorescent image based on the brightness of the fluorescent image measured by the brightness measurement unit 426. FIG. 12 shows an example having the same configuration in which a brightness measurement unit 426 and a brightness adjustment unit 427 are added to the first embodiment.

The brightness adjustment unit 427 adds a value calculated based on the brightness of the fluorescent image to the gradation values of all the pixels of the fluorescent image, for example, in order to increase the brightness of the fluorescent image such that the brightness of the fluorescent image is equivalent to that of the G-component image.

In the present embodiment, the blended image generation unit 421 generates the blended image using the fluorescent image of which the brightness has been adjusted by the brightness adjustment unit 427.

The larger the difference between the brightness of the G-component image and the brightness of the fluorescent image, the more the color tone of the superimposed image is different from the color tone of the normal light image. According to the present embodiment, by generating a blended image using the fluorescent image of which the brightness is adjusted so as to have the same brightness as that of the G-component image, it is possible to bring the color tone of the superimposed image closer to the color tone of the normal light image.

Figure 13:
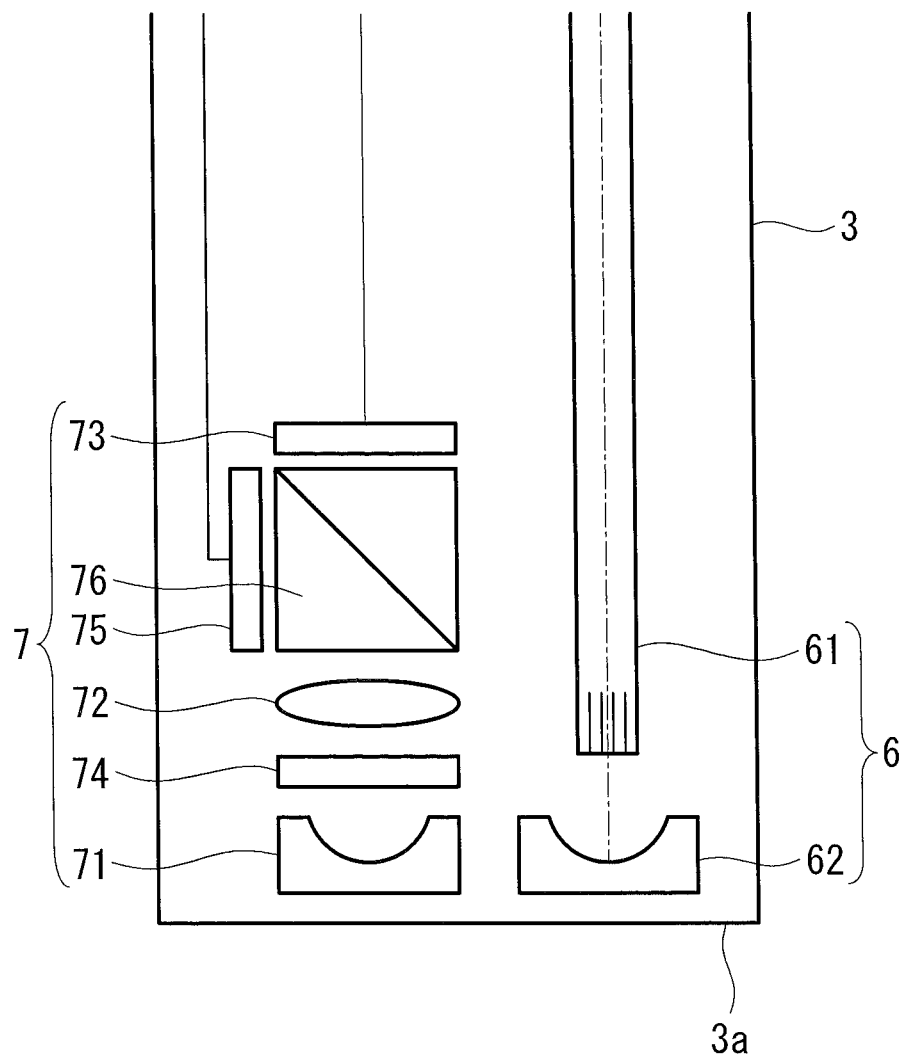
FIG. 13 is a partial configuration diagram showing a modification of an image acquisition unit in the endoscope device shown in FIG. 1.

It should be noted in the aforementioned first through fifth embodiments, the descriptions has been made regarding an arrangement in which the normal light and the excitation light are alternately irradiated to the biological tissue S, and the normal light image signal and the fluorescent image signal are alternately acquired by using a the single imaging sensor 73. Alternatively, the normal light and the excitation light may be simultaneously irradiated to the biological tissue S to acquire the normal light image signal and the fluorescent image signal at the same time. In this case, as shown in FIG. 13, the image acquisition unit 7 further includes another imaging sensor 75, and a beam splitter 76 that splits the light collected by the objective lens 71 into two beams and distributes them to the imaging sensor (normal light image acquisition unit) 73 and the image acquisition sensor (special light image acquisition unit) 75.

Descriptions has been made in the aforementioned first through fifth embodiments regarding an arrangement in which the fluorescent image is blended with the G-component image so that the fluorescent region are displayed in green in the superimposed image. The fluorescent image may be blended with the R-component image or the B-component image to generate a blended image.

Descriptions has been made in the aforementioned first through fifth embodiments regarding the excitation light that excites a fluorescent substance, as an example of the special light and the special light image. However, the special light and the special light image are not limited to these kinds. For example, an infrared light may be employed to acquire an infrared light image. Also, blue narrowband light and green narrowband light may be employed to acquire an NBI image.

From the above-described embodiments, the following inventions are derived.

The present invention provides an endoscope device including: a normal light image acquisition unit that acquires a normal light image by capturing an image of a subject irradiated with a broadband visible light; a special light image acquisition unit that acquires a special light image by capturing an image of the subject irradiated with a narrowband special light; a blended image generation unit that generates a blended image by combining one color component image from among a plurality of color component images constituting the normal light image and the special light image; and a superimposed image generation unit that generates a color superimposed image by combining the blended image generated by the blended image generation unit with another color component image from among the plurality of color component images, wherein the blended image generation unit generates the blended image by selecting a part of pixels from among the pixels of the one color component image, and by replacing the pixels of the selected part with corresponding pixels of the special light image, so that the pixels of the part of the one color component image are replaced with the corresponding pixels of the special light image such that the pixels of the one color component image and the pixels of the special light image are blended in a substantially uniform distribution over the entire blended image.

According to a present invention, the normal light image configured as a color image acquired by the normal light image acquisition unit is separated into a one color component image and another color component image. The separated one color component image is blended with the special light image acquired by the special light image acquisition unit, so as to generate the blended image. The superimposed image generation unit combines the generated blended image with another color component image, thereby generating a color image. As a result, a superimposed image in which the special light image is superposed on the normal light image is obtained.

In this case, such an arrangement does not perform processing of extracting only a part of the regions from the special light image, but the entire image is combined into the blended image approximately uniformly. Accordingly, such an arrangement allows all the regions of interest having gradation values in the special light image to be displayed on the superimposed image. Furthermore, by mixing the pixels of the one color component image and the pixels of the special light image as they are in the blended image, such an arrangement reduces change in the gradation values of the blended image with respect to the one color component image. In addition, the noise included in the special light image is reduced in the blended image. This allows the superimposed image to be generated with little color tone change and low noise with respect to the normal light image.

In the above-described invention, the blended image generation unit may have a blend pattern that defines an array of the pixels of the one color component image and the pixels of the special light image configured such that the pixels of the one color component image and the pixels of the special light image are alternately arrayed in a row direction and in a column direction in increments of a minimum repetition unit which is a unit having one pixel or a unit having a plurality of pixels, and wherein the blended image generation unit replaces the pixels of the part selected from the one color component image with the pixels of the special light image according to the array of the pixels of the blend pattern.

Such an arrangement provides an advantage of maintaining the color tone and an advantage of reducing noise in a stable manner.

In the above-described invention, the blend pattern may be a periodic sequence pattern in which the minimum repetition unit in the row direction and the minimum repetition unit in the column direction are different from each other.

With such an arrangement, in a region of interest having high gradation values in the special light image among the superimposed images, a pattern that corresponds to the periodic sequence pattern is displayed in colors of the one color component image that is combined with the special light image. Such a pattern can improve the distinguishability of the region of interest.

In the above-described invention, the blend pattern may be a square grid array pattern in which the minimum repetition unit in the row direction and the minimum repetition unit in the column direction are equal to each other.

With such an arrangement, it is possible to obtain a superimposed image in which change in the color tone, and noise are further reduced.

In the above-described invention, the endoscope device may further comprise a blend pattern setting unit that sets the blend pattern, wherein the blended image generation unit generates the blended image according to the blend pattern set by the blend pattern setting unit.

With such an arrangement, the blend pattern used for generating the blended image can be changed by the blended pattern setting unit.

In the above-described invention, the endoscope device may further comprise a contrast measurement unit that measures a contrast of brightness of the special light image, wherein the blend pattern setting unit sets the blend pattern such that the number of pixels that form the minimum repetition unit in the blend pattern increases as the contrast decreases based on the contrast measured by the contrast measurement unit.

When the gradation values of the region of interest are low and the contrast of brightness of the special light image is low, the distinguishability of the region of interest in the superimposed image is low. Therefore, by increasing the number of pixels that form the minimum repetition unit of the blend pattern, the size of the pattern displayed in the region of interest in the blended image is increased. Such an arrangement is capable of providing improved distinguishability of the region of interest even if it has low gradation values.

In the above-described invention, the endoscope device may further comprise a brightness measurement unit that measures brightness of the special light image, wherein the blend pattern setting unit sets the blend pattern such that the number of pixels that form the minimum repetition unit in the blend pattern increases as the brightness decreases based on the brightness measured by the brightness measurement unit.

In a case in which the special light image is dark, the distinguishability of the region of interest in the superimposed image is low. Therefore, by increasing the number of pixels that form the minimum repetition unit of the blend pattern, the size of the pattern displayed in the region of interest in the blended image is increased. Such an arrangement is capable of providing improved distinguishability of a region of interest even if it has low gradation values.

In the above-described invention, the endoscope device may further comprise: a brightness measurement unit that measures brightness of the special light image; and a brightness adjustment unit that adjusts the brightness level of the special light image based on the brightness measured by the brightness measurement unit, wherein the blended image generation unit generates the blended image using the special light image of which the brightness has been adjusted by the brightness adjustment unit.

When there is a large difference in the brightness between the special light image and the one color component image, this leads to a large difference in the color tone between the normal light image and the superimposed image. Therefore, by adjusting the brightness of the special light image, it is possible to generate a superimposed image having a color tone that is even closer to that of the normal light image.

The present inventions provide an advantage of generating a superimposed image with little change in color tone and low noise, such that all the regions of interest in the special light image are displayed.

REFERENCE SIGNS LIST 1 endoscope device
2 light source unit
421 blended image generation unit (blend pattern setting unit)
422 superimposed image generation unit
424 pattern size adjustment unit (blend pattern setting unit)
425 contrast measurement unit
426 brightness measurement unit
427 brightness adjustment unit
73 imaging sensor (normal light image acquisition unit, special light image acquisition unit)

The invention claimed is:
1. An endoscope device comprising:
a sensor configured to acquire:
a normal light image by capturing an image of a subject irradiated with a broadband visible light; and
a special light image by capturing an image of the subject irradiated with a narrowband special light; and
a processor configured to:
generate a plurality of component images from the normal light image, wherein each of the plurality of component images corresponds to one of a plurality of color components;
randomly select a part of a plurality of pixels of one component image corresponding to one color component of the plurality of component images of the plurality of color components;
generate a blended image by replacing the part of the plurality of pixels of the one component image randomly selected with corresponding pixels of the special light image; and
generate a color superimposed image by combining the blended image with at least another component image of another color component of the plurality of component images of the plurality of color components.

2. The endoscope device according to claim 1, wherein the processor is configured to:
measure brightness of the special light image;
adjust a brightness level of the special light image based on the brightness measured; and
generate the blended image using the special light image of which the brightness level has been adjusted.

3. A method comprising:
controlling a sensor to acquire:
a normal light image by capturing an image of a subject irradiated with a broadband visible light; and
a special light image by capturing an image of the subject irradiated with a narrowband special light;
generating a plurality of component images from the normal light image, wherein each of the plurality of component images corresponds to one of a plurality of color components;
randomly selecting a part of a plurality of pixels of one component image corresponding to one color component of the plurality of component images of the plurality of color components;
generating a blended image by replacing the part of the plurality of pixels of the one component image randomly selected with corresponding pixels of the special light image; and
generating a color superimposed image by combining the blended image with at least another component image of another color component of the plurality of component images of the plurality of color components.

4. An endoscope device comprising:
a sensor configured to acquire:
a normal light image by capturing an image of a subject irradiated with a broadband visible light; and
a special light image by capturing an image of the subject irradiated with a narrowband special light; and
a processor configured to:
generate a plurality of component images from the normal light image, wherein each of the plurality of component images corresponds to one of a plurality of color components;
select a part of a plurality of pixels of one component image substantially uniformly from the entirety of the one component image so there is no bias in the positions of the pixels selected in the one component image;
generate a blended image by replacing the part of the plurality of pixels of the one component image selected with corresponding pixels of the special light image; and
generate a color superimposed image by combining the blended image with at least another component image of another color component of the plurality of component images of the plurality of color components.

5. The endoscope device according to claim 4, wherein the processor is configured to:
    select the part of the plurality of pixels of the one component image based on a blend pattern that defines an array of the pixels of the one color component image and the pixels of the special light image such that the pixels of the one color component image and the pixels of the special light image are alternately arrayed in a row direction and in a column direction in increments of a minimum repetition unit which is a unit having one pixel or a unit having a plurality of pixels; and
    generate the blended image by replacing the part of the plurality of pixels of the one color component image selected with the corresponding pixels of the special light image according to the array of the pixels defined by the blend pattern.

6. The endoscope device according to claim 5, wherein the blend pattern is a periodic sequence pattern in which the minimum repetition unit in the row direction and the minimum repetition unit in the column direction are different from each other.

7. The endoscope device according to claim 5, wherein the blend pattern is a square grid array pattern in which the minimum repetition unit in the row direction and the minimum repetition unit in the column direction are equal to each other.

8. The endoscope device according to claim 5, wherein the processor is configured to:
    set the blend pattern; and
    select the part of the plurality of pixels of the one component image and generate the blended image based on the blend pattern set.

9. The endoscope device according to claim 8, wherein the processor is configured to:
    measure a contrast of brightness of the special light image; and
    set the blend pattern such that the number of pixels that form the minimum repetition unit in the blend pattern increases as the contrast decreases based on the contrast measured.

10. The endoscope device according to claim 8, wherein the processor is configured to:
    measure brightness of the special light image; and
    set the blend pattern such that the number of pixels that form the minimum repetition unit in the blend pattern increases as the brightness decreases based on the brightness measured.

* * * * *